United States Patent
Halleck et al.

[11] Patent Number: 5,549,113
[45] Date of Patent: Aug. 27, 1996

[54] APPARATUS AND METHOD FOR REMOTE MONITORING OF PHYSIOLOGICAL PARAMETERS

[75] Inventors: Michael D. Halleck, Northglenn; Donald N. James, Estes Park; Michael E. Halleck, Longmont, all of Colo.

[73] Assignee: I Am Fine, Inc., Bethesda, Md.

[21] Appl. No.: 380,259

[22] Filed: Jan. 30, 1995

Related U.S. Application Data

[63] Continuation of Ser. No. 187,787, Jan. 26, 1994, abandoned, which is a continuation of Ser. No. 973,299, Nov. 9, 1992, abandoned.

[51] Int. Cl.$^6$ .................. A61B 5/08; A61B 5/02
[52] U.S. Cl. .................. 128/671; 128/716; 128/721; 128/903
[58] Field of Search .................. 128/633, 664, 128/670–1, 700, 716, 719, 721–3, 903, 904; 340/539

[56] References Cited

U.S. PATENT DOCUMENTS

| | | |
|---|---|---|
| 3,572,316 | 3/1971 | Vogelman et al. . |
| 3,638,642 | 2/1972 | Heflin, Sr. .................. 128/903 X |
| 3,870,959 | 3/1975 | Wootton . |
| 3,915,154 | 10/1975 | Cosentino . |
| 4,365,636 | 12/1982 | Barker . |
| 4,367,458 | 1/1983 | Hackett . |
| 4,403,215 | 9/1983 | Hofmann et al. . |
| 4,422,458 | 12/1983 | Kravath . |
| 4,475,558 | 10/1984 | Brock . |
| 4,506,678 | 3/1985 | Russell et al. . |
| 4,580,575 | 4/1986 | Birnbaum et al. . |
| 4,675,656 | 6/1987 | Narcisse .................. 128/903 X |
| 4,681,111 | 7/1987 | Silvian . |
| 4,706,689 | 11/1987 | Man .................. 128/903 |
| 4,713,558 | 12/1987 | Russell et al. . |
| 4,765,340 | 8/1988 | Sakai et al. .................. 128/633 |
| 4,784,162 | 11/1988 | Ricks et al. . |
| 4,827,943 | 5/1989 | Bornn et al. . |
| 4,909,260 | 3/1990 | Salem et al. . |
| 5,022,402 | 6/1991 | Schieberl et al. . |
| 5,036,852 | 8/1991 | Leishman . |
| 5,086,391 | 1/1992 | Chambers . |
| 5,091,930 | 2/1992 | Shapiro . |
| 5,107,845 | 4/1992 | Guern .................. 128/664 |
| 5,133,346 | 7/1992 | Kulkarni .................. 128/716 X |
| 5,348,008 | 9/1994 | Bornn et al. . |

*Primary Examiner*—Angela D. Sykes
*Assistant Examiner*—Bryan Yarnell
*Attorney, Agent, or Firm*—Harold A. Burdick

[57] ABSTRACT

Apparatus and method are disclosed for monitoring selected physiological parameters of a subject, such as respiration and/or ECG information, and alerting a care giver at a remote location when an irregularity is recognized. The apparatus includes a sensor or sensors, a dual frequency, asynchronous transmitter unit for transmitting plural signals indicative of the sensed information, a local receiver/transmitter unit, and a remote receiver. The physiological parameters being monitored are sensed and processed to provide signals which are provided to a pair of transmitters. Transmission is selectively enabled at each transmitter, the first transmitting at a first frequency a signal indicative of real time monitored events and the second, under normal circumstances, transmitting, periodically, at a second frequency a signal indicative of monitored event count and updated subject status. When received at the local receiver, both signals are processed and retransmitted to the remote receiver where, if irregularity is indicated, the care giver is alerted.

31 Claims, 14 Drawing Sheets

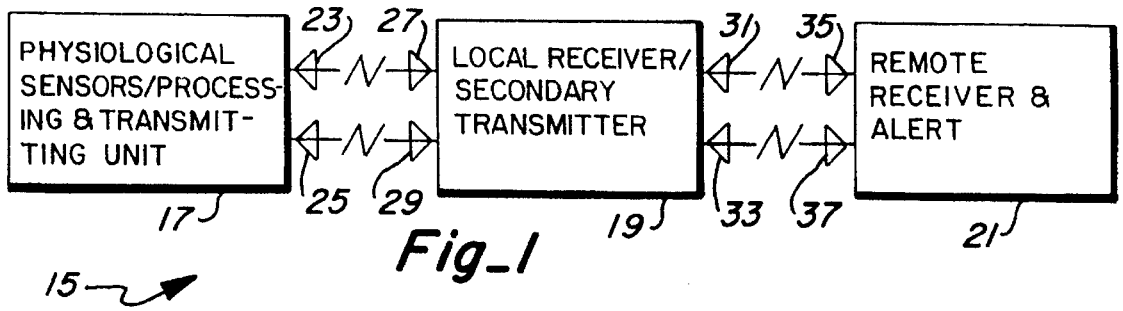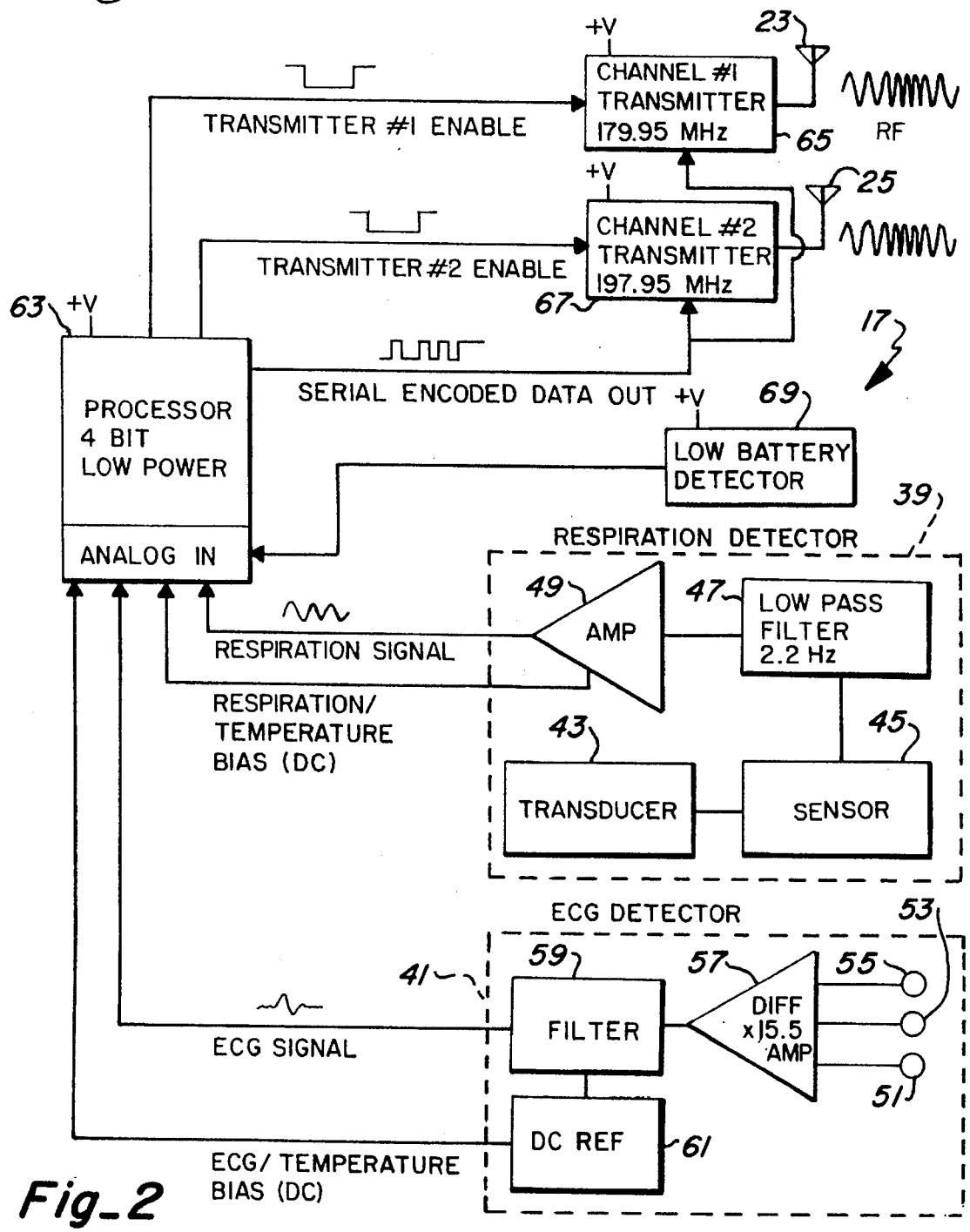

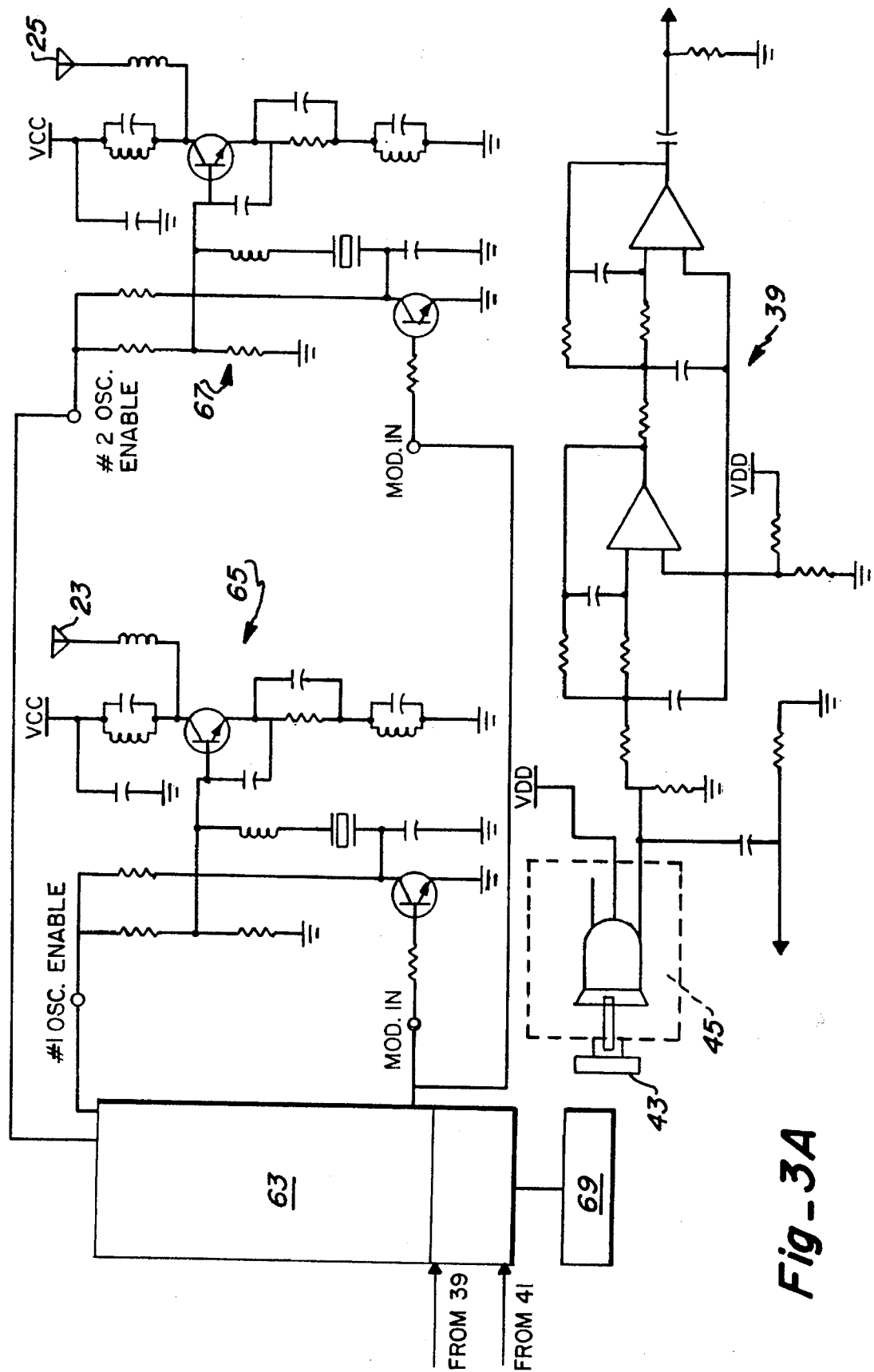
Fig._3A

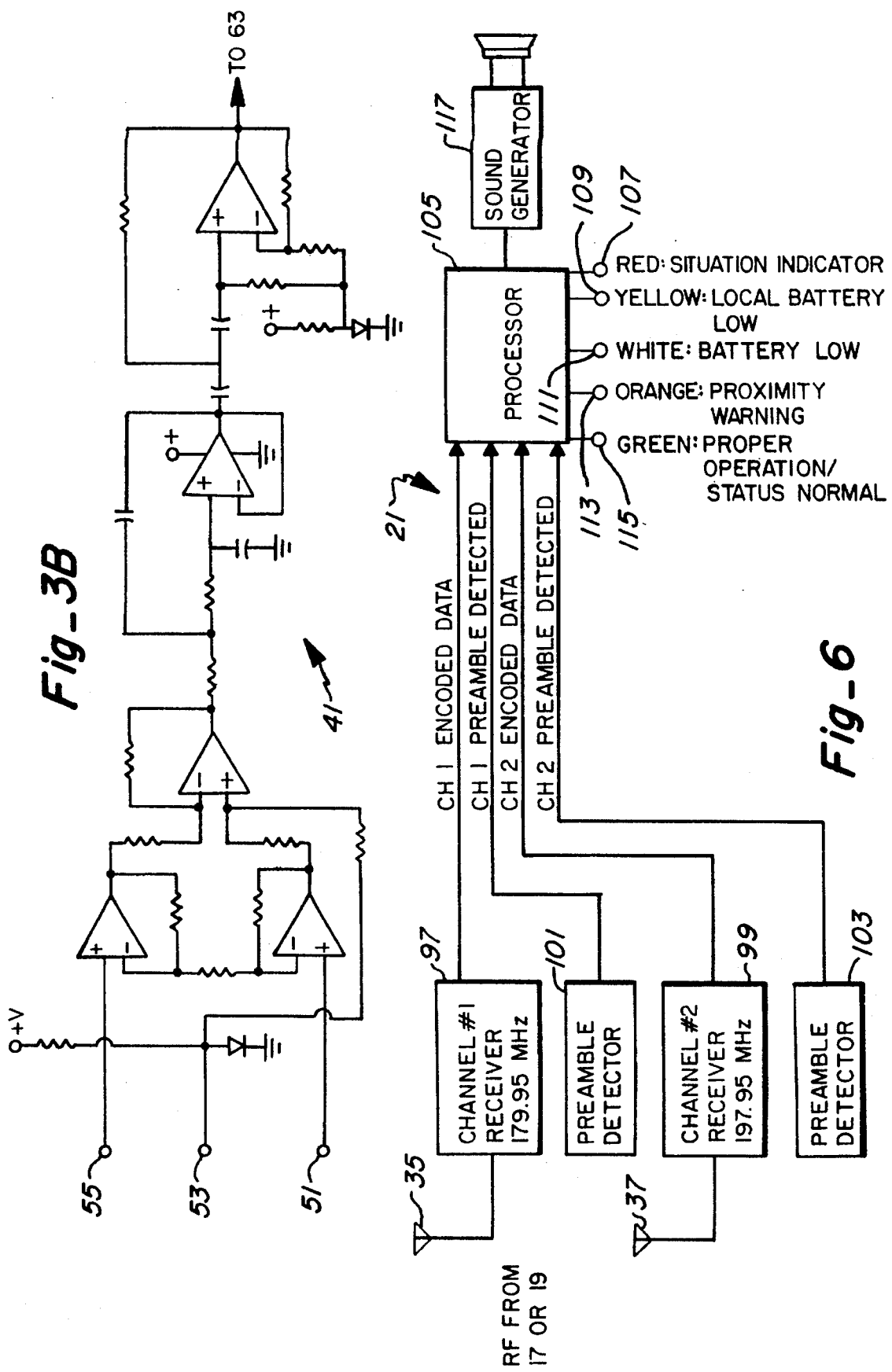

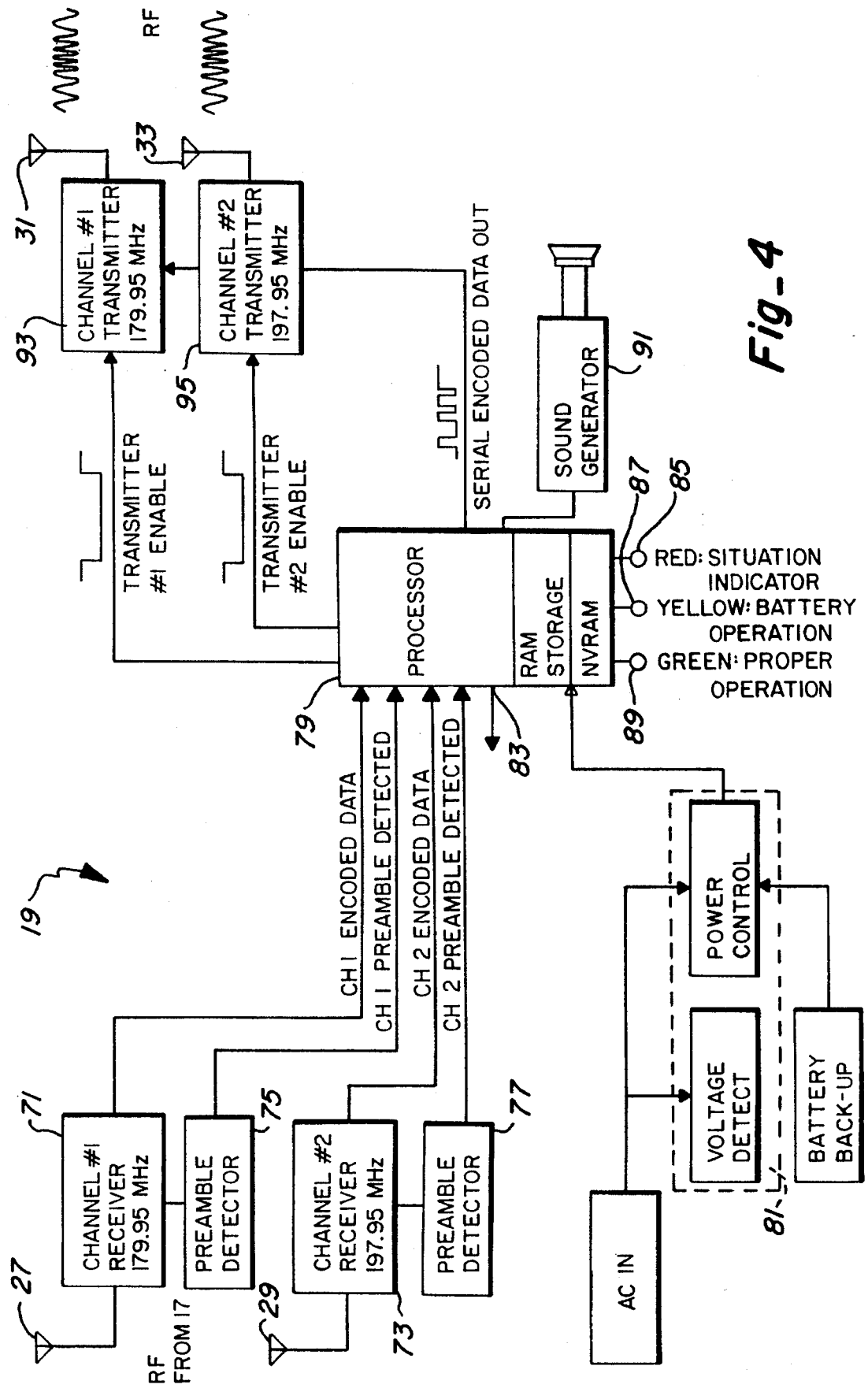
Fig._4

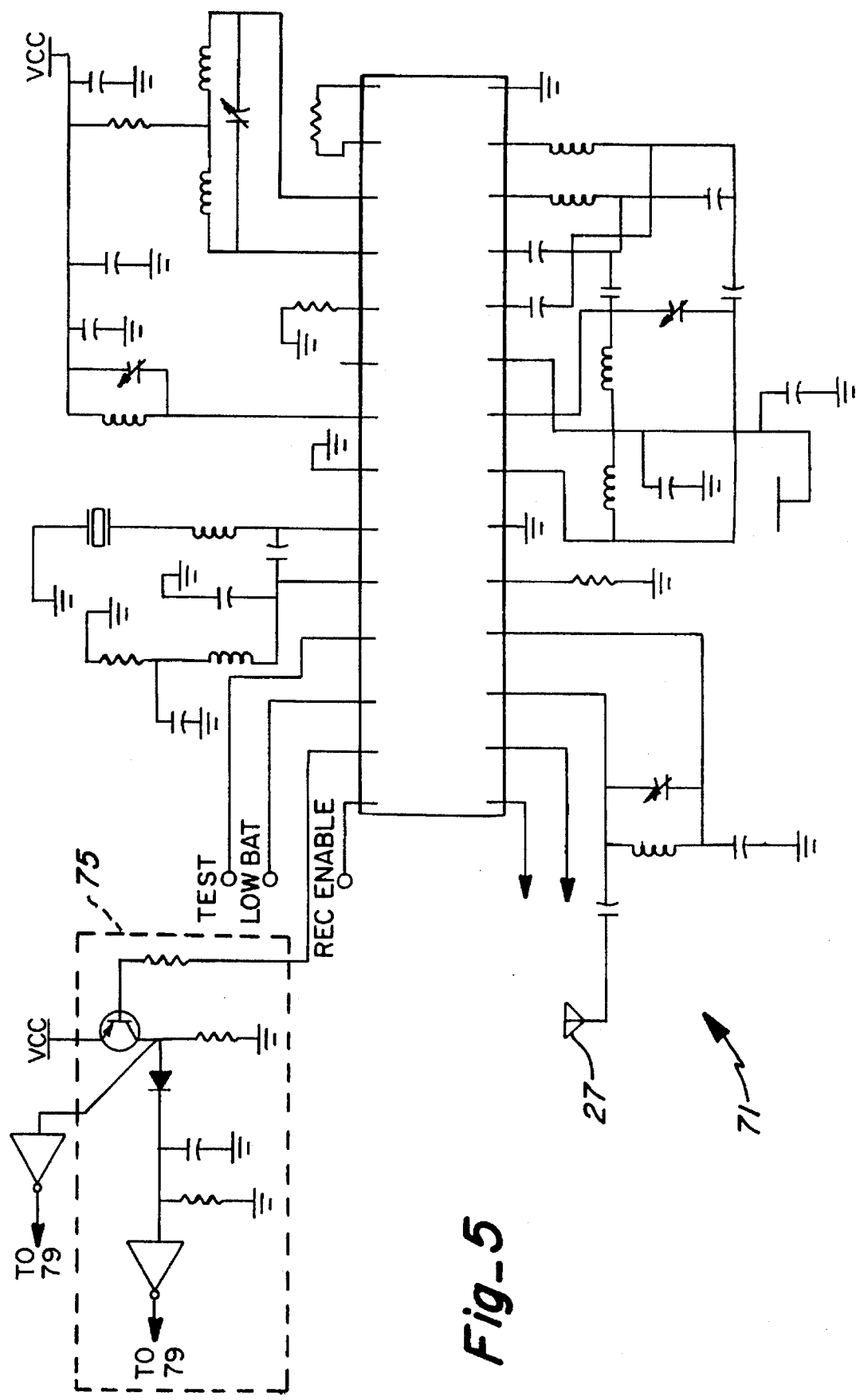
Fig_5

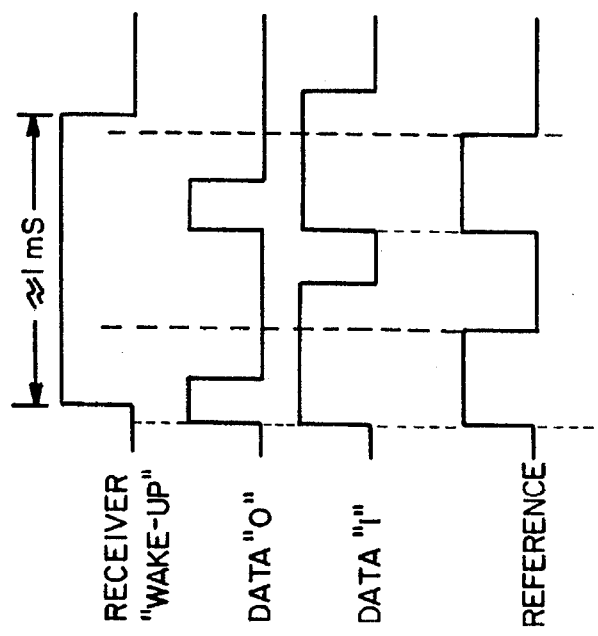
Fig_7A
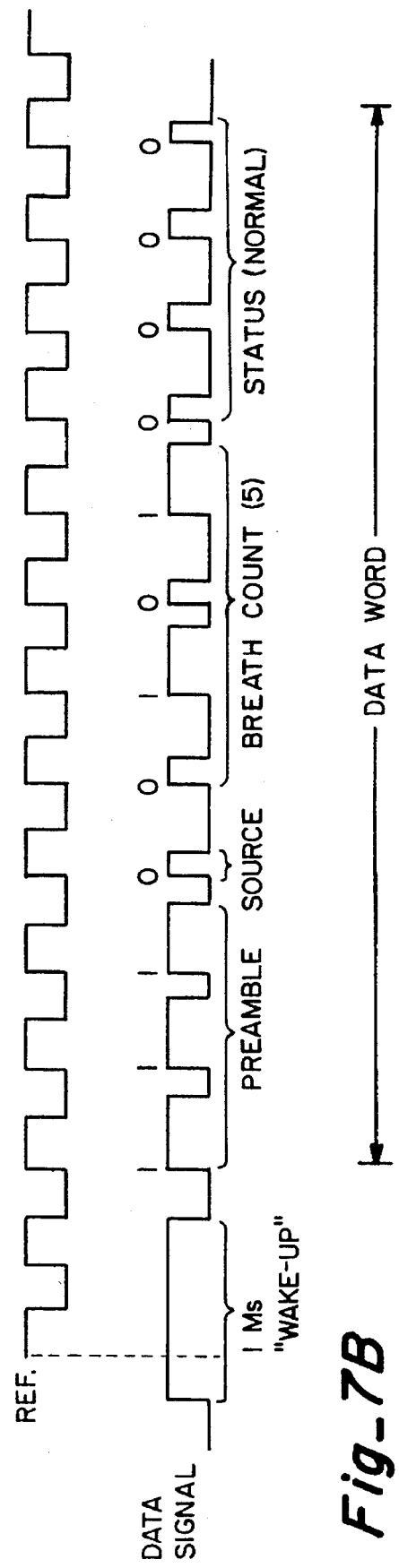
Fig_7B

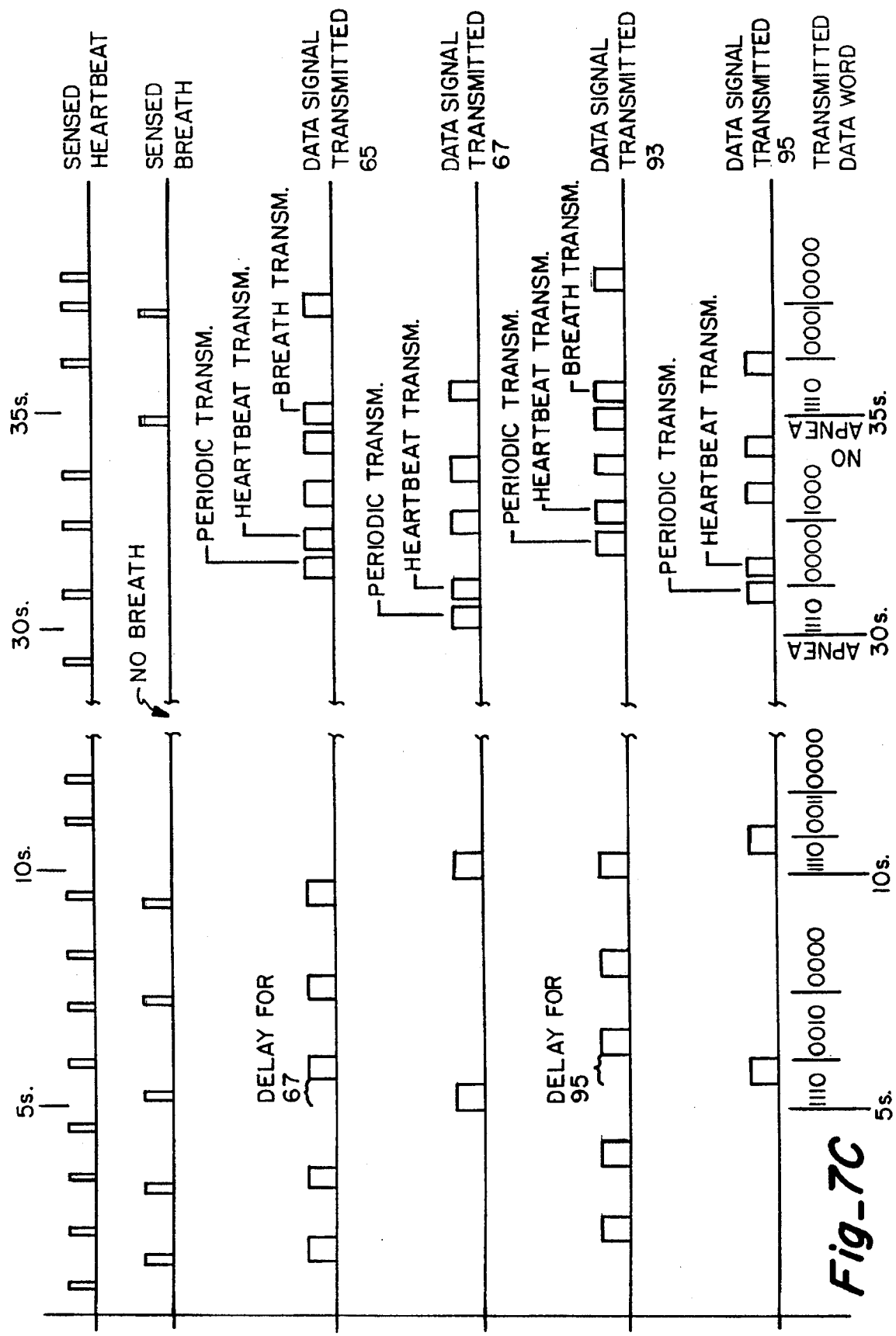
Fig_7C

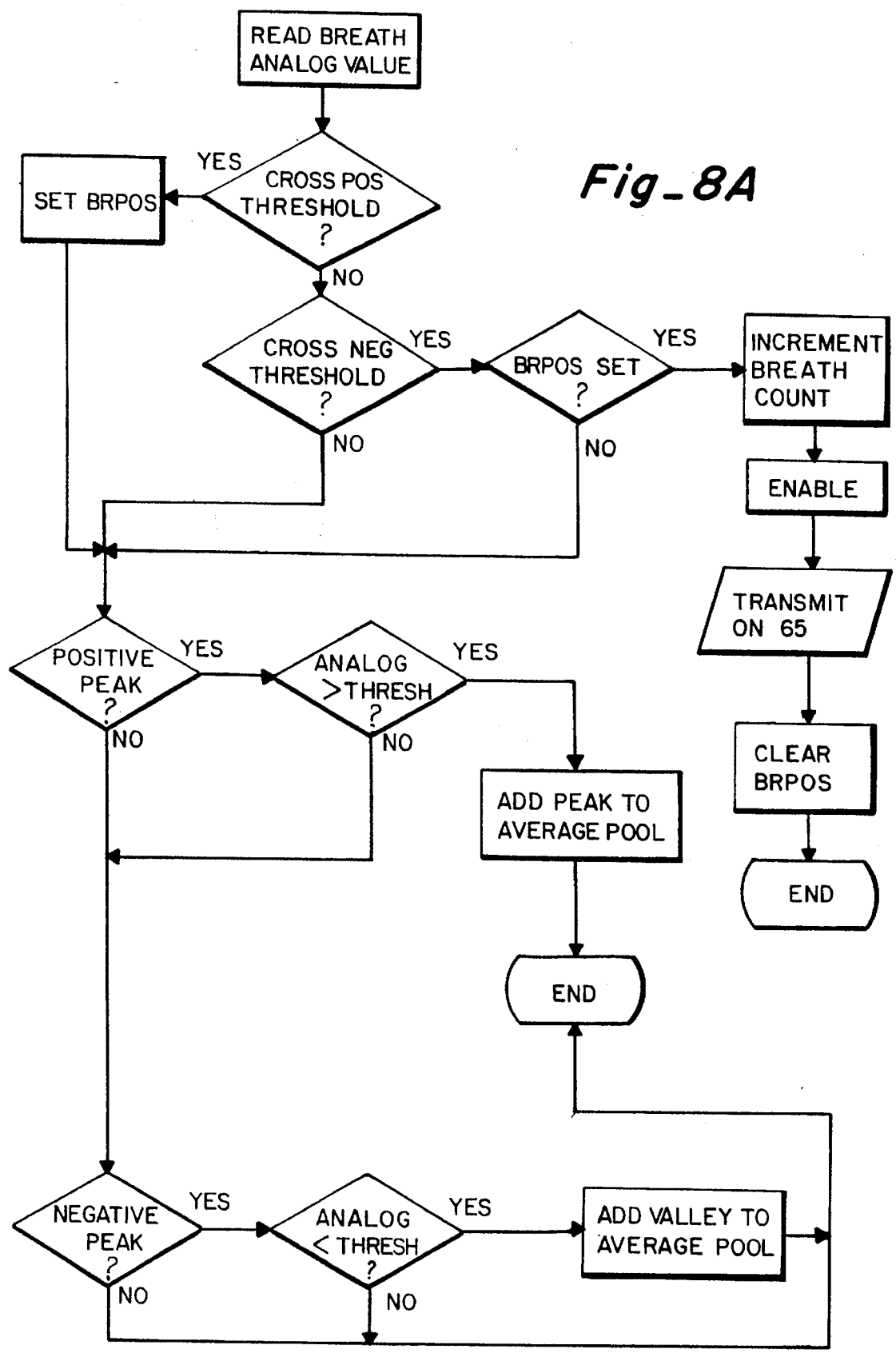
Fig_8A

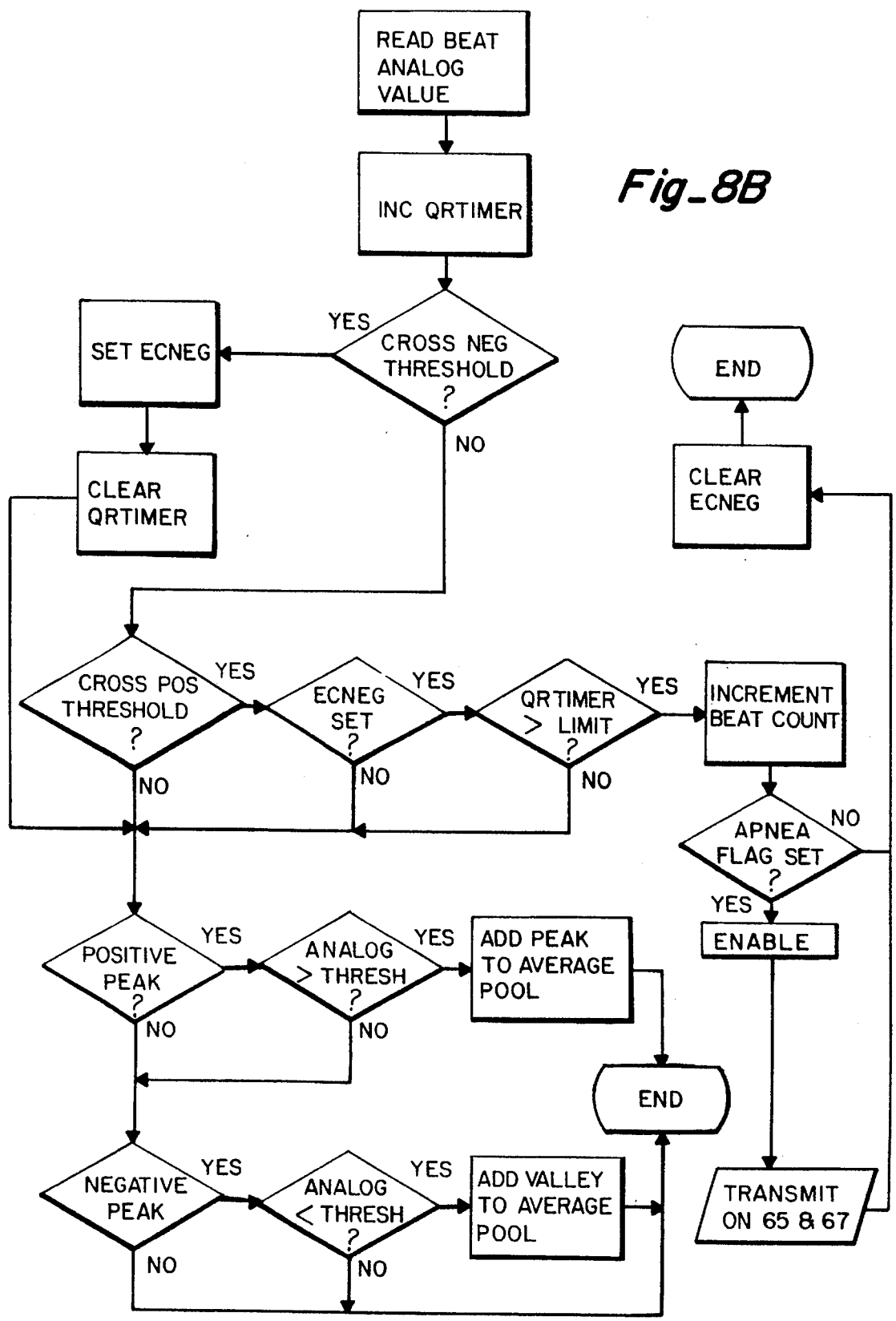

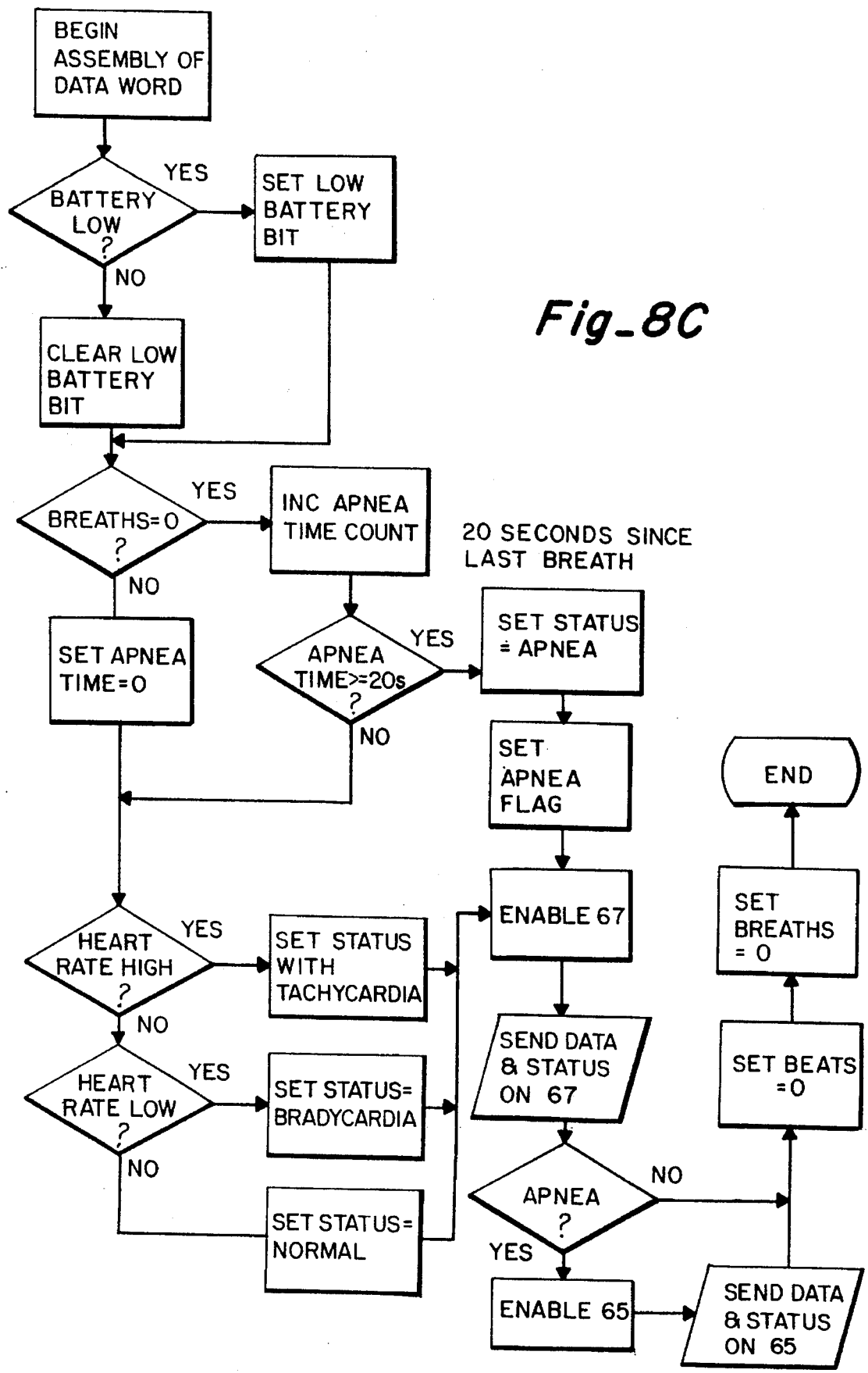
Fig_8C

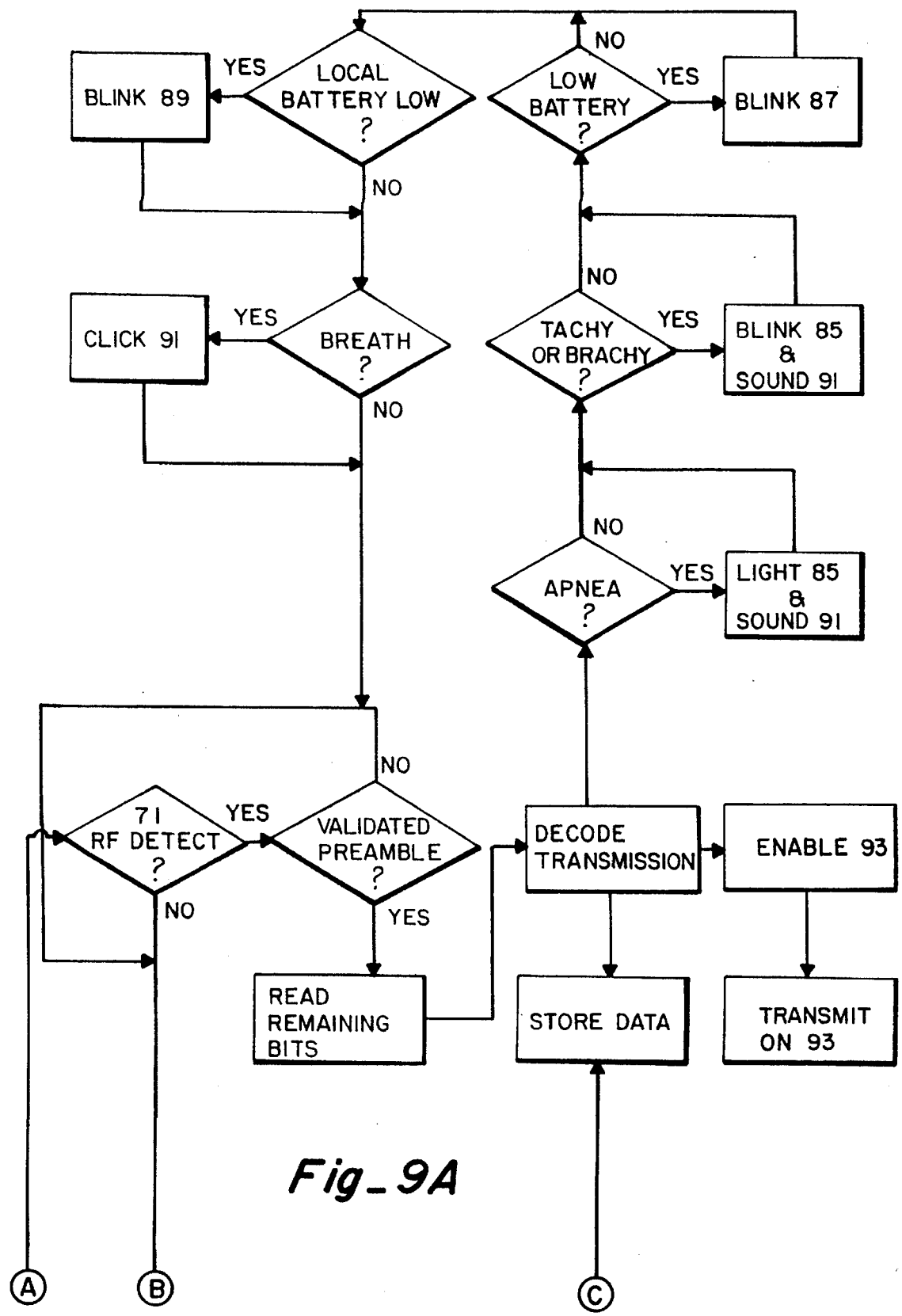
Fig_9A

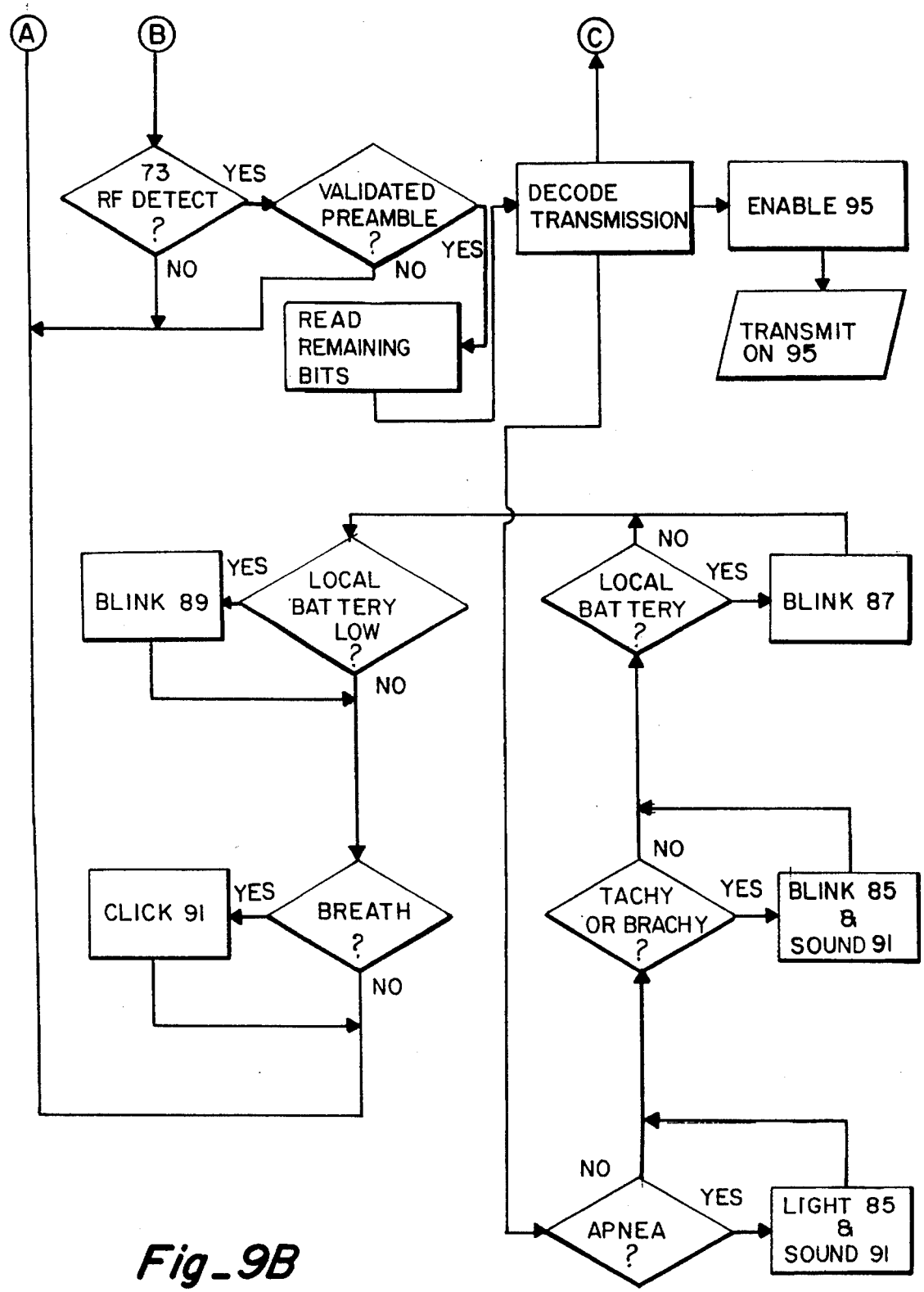
Fig_9B

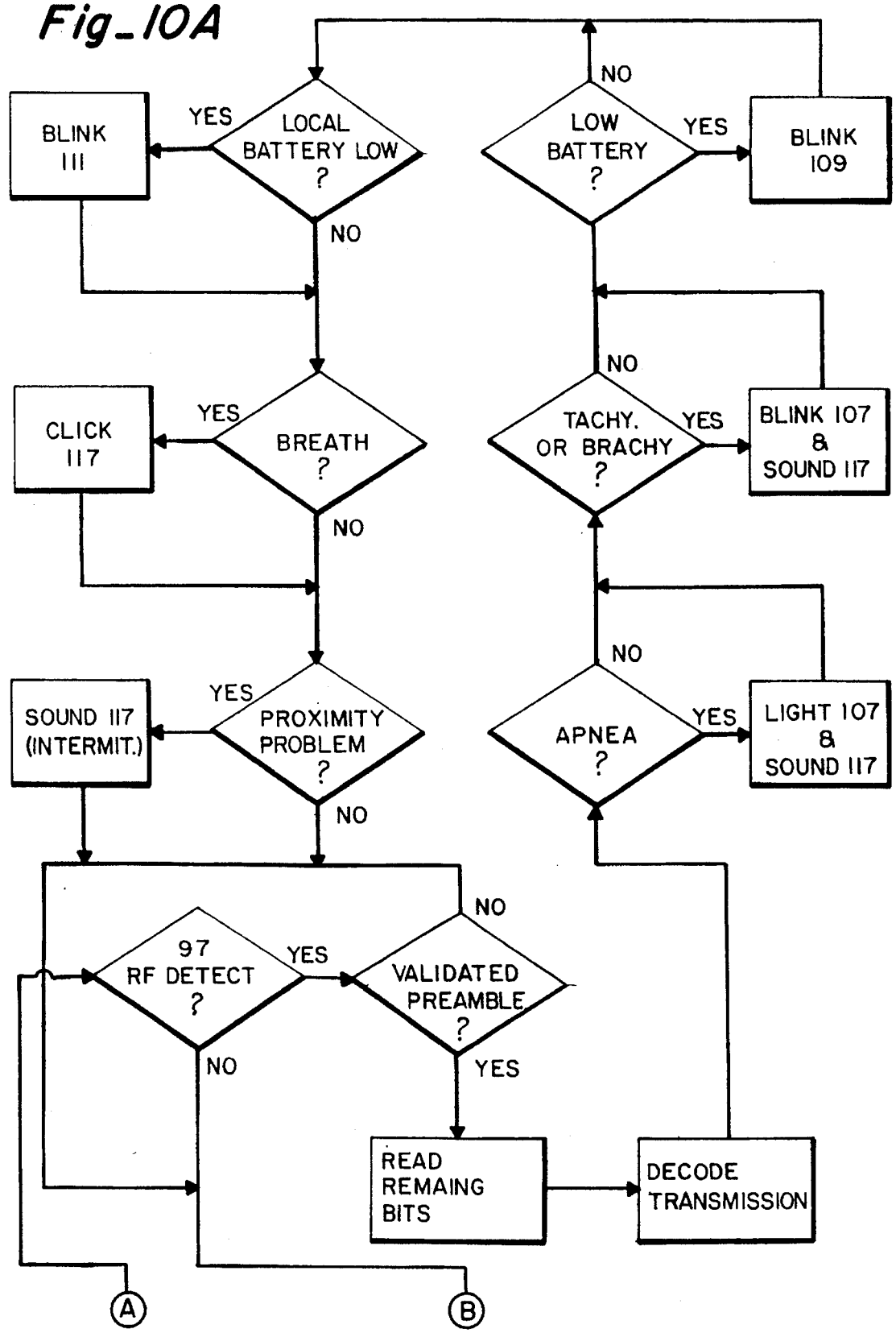
Fig_10A

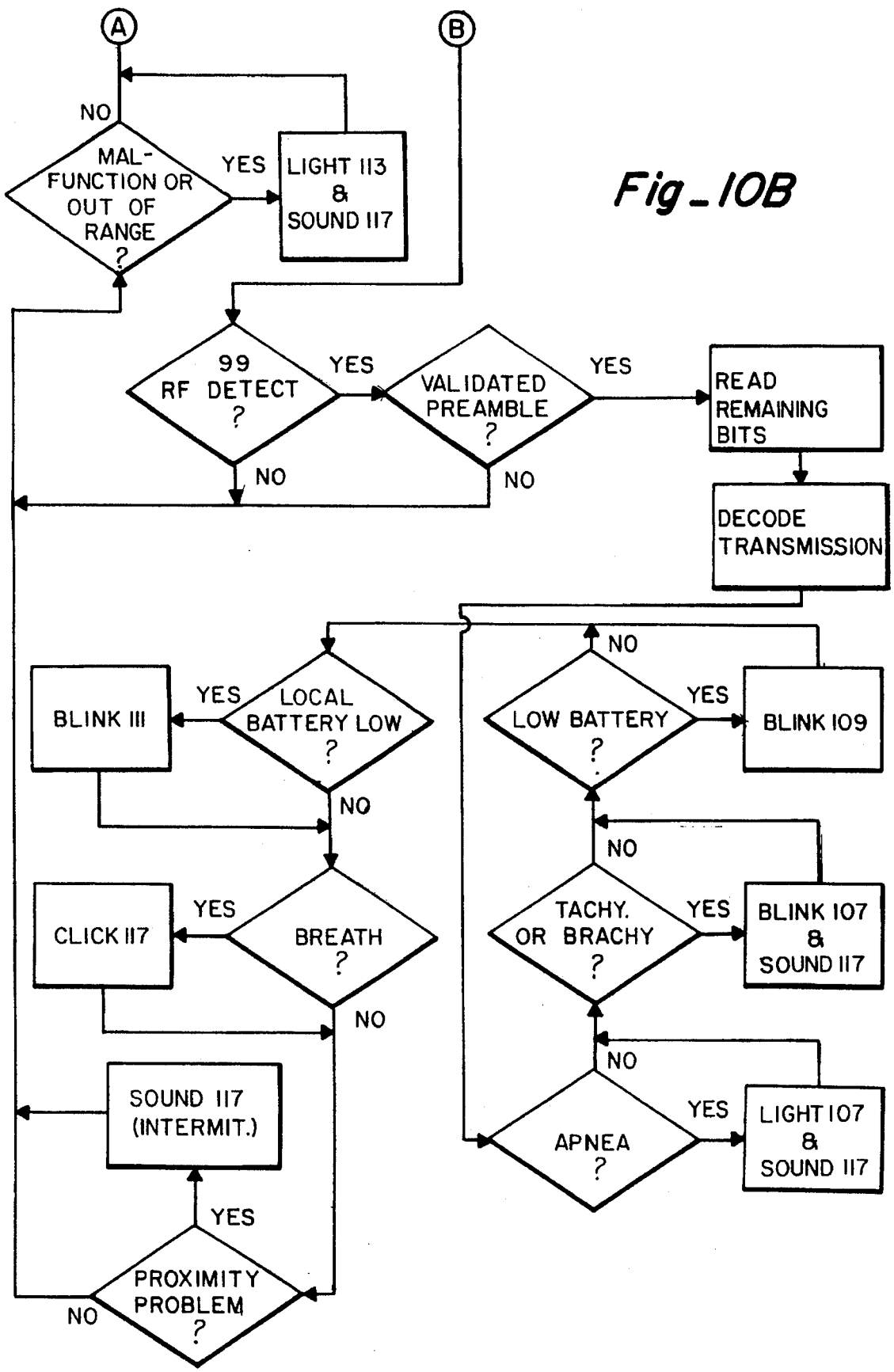
Fig_10B

APPARATUS AND METHOD FOR REMOTE MONITORING OF PHYSIOLOGICAL PARAMETERS

RELATED APPLICATION

This application is a continuation of U.S. patent application Ser. No. 08/187,787 filed on Jan. 26, 1994, now abandoned, and entitled "Apparatus And Method For Remote Monitoring Of Physiological Parameters" by Halleck et. al., which is a continuation of U.S. patent application Ser. No. 07/973,299 filed on Nov. 9, 1992 (now abandoned).

FIELD OF THE INVENTION

This invention relates to physiological monitors and monitoring methods, and, more particularly, relates to monitoring physiological parameters at one location and receiving monitored information at another.

BACKGROUND OF THE INVENTION

Patient monitors for monitoring various physiological characteristics of a subject have been heretofore suggested and/or utilized (see, in general, U.S. Pat. Nos. 5,036,852, 4,506,678 and 4,713,558), some including means of transmission to remote receivers (see U.S. Pat. No. 5,022,402) or multiple modes of data reporting (see U.S. Pat. No. 4,475, 558). Various emergency response systems, often utilizing multiple data transfer links, have also heretofore been suggested and/or utilized for linking a subject to a central response network (see U.S. Pat. Nos. 5,086,391, 5,091,930, and 5,128,979).

Such monitors and systems, however, have not addressed the need for on-site monitors which may be conveniently and comfortably used (i.e., which minimize discomfort of the subject), which can be used by untrained personnel, and which will reliably transfer information to, and thus alert, a care giver in a wide variety of situations and environments including, for example, subject disability (or in cases where the subject is sleeping and/or is an infant), transmission signal loss or distortion (due to data channel failure, transmission noise, stray signals, range limitations, or the like) and/or high noise environments.

While dual frequency transmitters and the like have been heretofore suggested and/or utilized in various settings (see, for example, U.S. Pat. Nos. 3,870,959, 4,367,458, 2,892,930 and 4,494,238), such transmitters have not been heretofore adapted for use in medical monitoring and/or do not in and of themselves resolve many of the above-addressed needs. Thus, improvements directed to increasing the reliability, comfort and ease of use of monitors employed to remotely monitor selected physiological parameters could still be utilized.

SUMMARY OF THE INVENTION

This invention provides improved apparatus and methods for remote monitoring of selected physiological parameters of a subject, and in particular provides such apparatus and methods for monitoring a subject's respiration. The apparatus and methods employ dual frequency, asynchronous transmissions for data transfer between the subject and the care giver, with information regarding the monitored physiological parameter being carried in both transmissions but communicating at some times different basic information (i.e. event information versus event count information and/or subject status information) while communicating at other times redundant information. Thus loss of one transmission does not result in a loss of data which is relied upon to alert a care giver to an irregularity (such as apnea) requiring attention.

The apparatus includes a sensor, such as a respiration sensor and/or heart rate sensor, a processor for receiving sensed physiological information and processing the information to provide an output indicative thereof, and first and second transmitters for receiving the output from the processor and for providing, asynchronously, first and second transmissions indicative thereof, each at a different frequency. The output from the processor is preferably a data signal, or word, including sensed physiological event count data conveying the number of sensed physiological events occurring during a predetermined period. The first transmission is provided after each sensed physiological event while the second transmission is provided after each predetermined period.

The processor selectively issues enabling signals to the transmitters thus controlling the flow and priority of the asynchronous transmissions. A local receiving unit, preferably including first and second receivers and dual processing channels, receives and processes the transmissions and provides an indication of the subject's status. The local receiving unit includes a transmitting unit, again preferably dual frequency, providing transmissions indicative of the sensed information and/or subject status, and which is effective over a greater distance than the first and second transmitters, these transmissions being received by an alerting unit, for example a pager.

It is therefore an object of this invention to provide improved apparatus and methods for remote monitoring of physiological parameters.

It is another object of this invention to provide apparatus for monitoring respiration which may be conveniently and comfortably used, can be used by untrained personnel, and which will reliably transfer information to, and thus alert, a care giver in a wide variety of situations and environments.

It is still another object of this invention to provide apparatus and methods for remote monitoring of physiological parameters which employ dual frequency, asynchronous transmissions for data transfer between the subject and the care giver.

It is yet another object of this invention to provide apparatus and methods for remote monitoring of physiological parameters wherein information regarding the monitored physiological parameter is carried in dual transmissions, with each transmission communicating at some times different basic information (i.e. individual event occurrence versus event count information and/or subject status information) while communicating at other times redundant information.

It is still another object of the invention to provide an apparatus for enabling remote monitoring at a receiving unit of a selected physiological parameter, the apparatus being used in association with a sensor for sensing the selected physiological parameter of a subject, the apparatus including a processing unit for receiving information indicative of the selected physiological parameter from the sensor and processing the information to provide output indicative of the information, a first transmitter for receiving the output from the processing unit and providing a first transmission indicative thereof, and a second transmitter operable asynchronously and at a different frequency from the first transmitter for receiving the output from the processing unit and providing a second transmission indicative thereof.

It is another object of this invention to provide an apparatus for enabling remote monitoring at a receiving unit of a selected physiological parameter wherein output from a processing unit connected with a sensor is a data signal including sensed physiological event count data conveying the number of sensed physiological events occurring during a predetermined period, and wherein a first transmitter provides a first transmission indicative of the data signal after sensing of each physiological event and wherein a second transmitter provides a second transmission indicative of the data signal after each predetermined period.

It is yet another object of this invention to provide an apparatus for remote monitoring of respiration of a subject comprising a respiration sensor associable with the subject to provide an output indicative of respiration of the subject, a processing unit for receiving the output from the sensor and processing the output to provide a first signal indicative of the output and for selectively providing second and third signals, a first transmitter for receiving the first and second signals from the processing unit and providing a first transmission indicative of the first signal as an output therefrom when enabled by receipt of the second signal, a second transmitter for receiving the first and third signals from said processing unit and providing a second transmission indicative of the first signal as an output therefrom when enabled by receipt of the third signal, a receiver for receiving the transmissions from the first and second transmitters and utilizing the transmissions to provide an indication of respiration of the subject.

It is still another object of this invention to provide an apparatus for remote monitoring of respiration and at least one additional physiological parameter of a subject comprising means for sensing respiration and at least one additional physiological parameter of the subject and providing an output indicative thereof, a processing unit for receiving the output and providing a signal indicative of the output, a dual frequency transmitter providing, asynchronously, first and second transmissions indicative of the signal from the processing unit, the first and second transmissions being effective within a first distance, a receiving and retransmitting unit for receiving the transmissions from the transmitter and providing a third transmission indicative of the signal from the processing unit, the third transmission being effective within a second distance greater than the first distance, and an alerting unit for receiving the third transmission and providing an indication to a care giver of subject status.

It is yet another object of this invention to provide a method for remote monitoring of a selected physiological parameter of a subject including the steps of sensing the selected physiological parameter, processing the sensed physiological parameter to provide a signal indicative of the sensed physiological parameter, providing a first transmission indicative of the signal at a first frequency, providing a second transmission indicative of the signal asynchronously and at a different frequency from the first transmission, and receiving the transmissions remotely from the subject.

It is still another object of this invention to provide a method for remote monitoring of respiration of a subject comprising the steps of sensing each breath of the subject, providing a signal indicative of each sensed breath, utilizing the signals to provide a count of sensed breaths during selected time periods, emitting a transmission indicative of each signal, emitting a transmission indicative of the count after each time period, receiving the transmissions remotely from the subject, and processing the received transmissions to provide an alert if respiration irregularity is indicated.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a block diagram of the apparatus of this invention;

FIG. 2 is a block diagram of the sensor/transmitter unit of the apparatus of FIG. 1;

FIGS. 3A and 3B are schematic diagrams of the sensor/transmitter unit of FIG. 2;

FIG. 4 is a block diagram of the local receiver/secondary transmitter of the apparatus of FIG. 1;

FIG. 5 is a schematic diagram of the receiver and preamble detection circuit of FIG. 4;

FIG. 6 is a block diagram of the remote receiver and alerting unit (pager) of the apparatus of FIG. 1;

FIGS. 7A through 7C are graphic representations of output data formation and exemplary transmissions of the apparatus of this invention;

FIGS. 8A through 8C are flow charts illustrating operation of the sensor/transmitter unit of FIG. 2;

FIGS. 9A and 9B are flow charts illustrating operation of the local receiver/secondary transmitter of FIG. 4; and FIGS. 10A and 10B are flow charts illustrating operation of the remote receiver and alerting unit of FIG. 6.

DESCRIPTION OF THE INVENTION

The preferred embodiment of the overall apparatus 15 of this invention (a plurality of communicating units, various aspects of this invention residing in one or more of the units) is diagrammatically illustrated in FIG. 1. The overall apparatus (or system) includes physiological sensors/processing and transmitting unit 17, local receiver/secondary transmitter unit 19 and remote receiver and alerting unit (for example, a pager) 21. Unit 17 includes dual transmission sources 23 and 25, unit 19 includes dual receiving antennas 27 and 29 and dual transmission sources 31 and 33, and unit 21 includes dual receiving antennas 35 and 37.

Unit 17, as shown in FIGS. 2 and 3A and 3B, is battery powered, preferably self contained, and is directly mountable on the subject. The unit includes physiological detectors 39 and 41, for sensing and processing respiration and ECG, respectively (other or different physiological detectors could be utilized, for example to detect body temperature, various organ functions, pulse oximetry or the like). Respiration detector 39 includes respiration transducer 43, pressure sensor 45, low pass filter 47 and amplifier 49 and provides an output wave form indicative of each breath of the subject as well as a DC bias signal to maintain baseline.

ECG detector 41 includes electrodes 51, 53 and 55 connected to amplifier 57. The signal from amplifier 57 is filtered at band pass filter 59 (6 to 18 Hz) to provide an output wave form indicative of heart beats of the subject. DC reference generator 61 is provided for generating a bias signal to maintain baseline. The output signals from detectors 39 and 41 are input to processor 63 (for example, a four bit, low power processor) connected with the detectors, where the respiration signal and ECG signal are digitally processed. The output from processor 63 is a serially encoded data stream (a data signal, or word) conveying data indicative of respiration and heart rate (as more fully set forth herein below).

Processor 63 is connected with transmitters 65 and 67 to provide both transmitters with the data signal as well as with independent transmitter enable signals. Low battery detection circuit 69 is connected with processor 63 and provides information indicative of battery status for incorporation into the data signal.

Transmitters 65 and 67 (as schematically illustrated in FIG. 3A) are operated at different, non-harmonicly related, frequencies (for example, transmitter 65 at 179.95 MHz and transmitter 67 at 197.95 MHz). The digital data signal is transmitted FSK with direct frequency modulation of the carrier at a total deviation of 6 to 10 KHz (preferably 8 KHz). Transmission range for transmitters 65 and 67, when used in system 15, need only be about 5 meters or less.

Turning to FIGS. 4 and 5, local receiver/secondary transmitter unit 19 includes tuned receivers 71 and 73 (which in most regards are similar and illustrated in FIG. 5 with respect to receiver 71) for receiving different ones of the transmissions from transmitters 65 and 67. Preamble detection circuits 75 and 77 are connected with receivers 71 and 73, respectively, and serve to validate the signals as ones emitted by transmitters 65 and 67 (as more fully set forth hereinafter). The output from circuits 75 and 77 (a signal indicating validity or not of the received transmission) is coupled to processor 79, which is also connected with receivers 71 and 73 to receive the received transmissions (including the encoded data signals).

Unit 19 is preferably an AC powered unit with battery backup (controlled by voltage detecting and power control circuit 81) for occasions of local power failure. Processor 79 includes operational memory (RAM storage) and nonvolatile memory (NVRAM) for storage of data signals as well as time stamping of critical events such as turning on and off of unit 19, AC power interruptions, occurrences of apnea, irregular heart rate activity and the like. Such stored information can thus later be retrieved utilizing auxiliary port 83.

Processor 79 is connected with LED readouts 85, 87 and 89 and local sound generator unit 91 providing information, as more fully discussed hereinafter, to a care giver. The output of processor 79 (again the data signals received by unit 19) is coupled to secondary transmitters 93 and 95 for retransmission to unit 21 when enabled by independent enabling signals received from processor 79. The arrangement and operation of transmitters 93 and 95 is substantially the same as heretofore discussed with respect to transmitters 65 and 67, with the exception that the transmission range of transmitters 93 and 95 is substantially greater (for example, accommodating effective transmissions of about 30 meters or more).

Unit 21, illustrated in FIG. 6, is a compact, battery powered receiving and processing unit maintained in the possession of the care giver, and includes receivers 97 and 99, preamble detection circuits 101 and 103 and processor 105, configured in substantially the same way and for the same purposes as receivers 71 and 73, circuits 75 and 77, and processor 79. Processor 105 is connected with LED readouts 107, 109, 111, 113, and 115 and sound generator unit 117 for purposes of alerting and informing the care giver with respect to both the monitored physiological parameter and equipment status.

FIGS. 7A through 7C illustrate the data encoding scheme utilized in processors 63 and 79 (FIG. 7A), a sample of a data signal (FIG. 7B), and exemplary transmissions (FIG. 7C) from units 17 and 19. The data signal is a 12 bit data word including a 3 bit valid signal identification, or preamble, a one bit source identification (utilized primarily at unit 21 to indicate whether the transmission is from unit 17, when in range, or unit 19), a 4 bit physiological event count (breaths or heart beats for example) data signal, and a 4 bit status signal (conveying subject status with respect to the monitored physiological event such as apnea, tachycardia, bradycardia, status normality or the like, and system status such as low battery conditions or the like). Data words not preceded by a wake-up signal generated in response to the enable signals from processors 63 or 79 are not received.

Turning now to FIGS. 7C, 8A through 8C, 9A, 9B 10A and 10B, the operation of apparatus 15 will be described with reference to the programming of processors 63, 79 and 105, respectively. Processor 63 periodically samples (for example, every one-hundredth of a second) the breath rate analog value (determined in accord with the positive and negative threshold values established and adjusted as shown in FIG. 8A) of the respiration signal received from detector 39. If the value exceeds the positive threshold value, the flag indicating positive threshold crossing (BRPOS) is set and the value is utilized for further evaluation and adjustment, if necessary, of the positive value threshold. If not, and if the value crosses the negative threshold value, and if BRPOS has been previously set, the breath count is incremented by one, transmitter 65 is sent an enabling signal by processor 63, the last established data word is transmitted on transmitters 65, and BRPOS is cleared.

If BRPOS was not previously set, the value is utilized for further evaluation and adjustment, if necessary, of the negative value threshold. If the analog value read does not cross the positive threshold or the negative threshold, the value is utilized to further evaluate the positive and negative value thresholds.

Likewise, processor 63 periodically samples (for example, every one-hundredth of a second) the heart beat analog value (again as established by the positive and negative threshold evaluation scheme shown in FIG. 8B) of the ECG signal received from detector 41. At every sample, a timer is incremented (by one one-hundredth of a second) for purposes of measuring time between a falling (Q) wave and a rising (R) wave (QRTIMER in FIG. 8B). If the value crosses the negative threshold value, a flag (ECNEG) indicating crossing of the negative threshold value is set, QRTIMER is cleared, and the value is utilized for further evaluation and adjustment, if necessary, of the negative value threshold. If not, and if the positive threshold value is not exceeded, the value is utilized only for further evaluation of the positive and negative value thresholds.

If the negative threshold value is not crossed, and the positive value is exceeded, and further if ECNEG has been set and the time counted by incrementing QRTIMER is greater than an established limit (indicating an average time between Q and R threshold), a heart beat is indicated and the beat count is incremented by one. If the apnea flag (discussed hereinafter) has not been set, ECNEG is cleared and the routine ends. If the apnea flag has been set, transmitters 65 and 67 are enabled by a signal from processor 63, the last established data word is transmitted by transmitters 65 and 67, and ECNEG is cleared.

If, in the case where the negative threshold is not crossed and the positive threshold value is exceeded, either ECNEG is not set or the time counted by incrementing QRTIMER is less than the established limit, the value is utilized for further evaluation of the positive value threshold.

Turning now to FIG. 8C, a data word is assembled by processor 63 (for example, every five seconds). The preamble signal, source signal, and physiological event count signal (in this case, the number of breaths taken by the subject in the last 5 seconds as taken from the incremented breath count in FIG. 8A) are assembled. If the battery is low, the battery low bit of the status signal is set. If not, it is cleared.

If the number of breaths since the last data word was assembled equals zero, a timer is incremented by 5 seconds, and if the incremented time is greater than an established threshold (for example, 20 seconds) the apnea flag and bit (of the status signal) are set, transmitters 65 and 67 are each sent an enabling signal, the data signal is transmitted on both transmitters (as discussed heretofore with respect to FIG. 8B, as long as the apnea flag is set each heartbeat detected will generate a signal on transmitters 65 and 67, an updated data signal also being transmitted every five seconds on both transmitters), and incremented heart beat count and breath count are set at zero.

If the incremented time is less than the established threshold, or if the number of breaths since the last data word was assembled is greater than zero (whereupon the incremented time is set at zero), if the number of heart beats either exceed a preset average heart rate range or drop below the range the appropriate bit of the status signal is set. If heart rate is within the normal range, a status normal bit of the status signal is set. Transmitter 67 is then sent an enabling signal from processor 63, a transmission is emitted, and incremented heart beat count and breath count are set at zero.

As illustrated in FIGS. 9A and 9B, processor 79 of local receiver/secondary transmitter unit 19 continually samples for detected RF transmissions at receivers 71 and 73. If an RF signal is detected at receiver 71, and if the preamble was validated by preamble detection circuit 75 the remaining bits (after the preamble) of the data word are read, the transmission is decoded (and the data word is reassembled), and a signal from processor 79 enables transmitter 93 for retransmission of the data signal to remote receiver unit 21.

If apnea is indicated (by a status bit), LED 85 is lit and sound generator 91 sounds an alarm. If either tachycardia or bradycardia is indicated by a status bit, LED 85 is caused to blink and sound generator 91 sounds an alarm. If a status bit indicates a low battery at unit 17, LED 87 is caused to blink. If the local transmitter battery is in use and is low, LED 89 is caused to blink. If a breath is detected (as would normally be the case when a transmission is received by receiver 93) sound generator 91 issues a click. Thereafter, the received data word is stored in memory.

After date storage, or where either no RF signal is detected or a non-validated transmission is detected, receiver 73 is checked for receipt of an RF signal. If no RF signal is detected, or if a non-validated transmission is detected, processor 79 returns to sample receiver 71 for detection of an RF signal. If a validated preamble is detected by preamble detection circuit 77, the remaining bits of the received data word are read, the transmission is decoded (and the data word is reassembled), and a signal from processor 79 enables transmitter 95 for retransmission of the data signal to remote receiver unit 21.

Thereafter the data word is analyzed, responded to and stored as heretofore discussed with respect to transmissions received by receiver 93, and processor 79 again samples for detection of an RF signal on receiver 71.

As illustrated in FIGS. 10A and 10B, the sampling routine conducted by processor 105 of remote receiver and alerting unit 21 is similar in most regards to that shown in FIGS. 9A and 9B except that no retransmission normally occurs (though a number of data links could be provided) and data would not necessarily be stored in memory of processor 105. In addition, if there is a system malfunction or range problem (i.e. where no valid or readable signal is received after a preselected time period because unit 21 is out of range or because of a system malfunction) LED 113 is caused to blink and sound generator 117 issues a signal. Also, if a proximity problem is indicated in either of the received transmissions (i.e., where transmissions are received in excess of every five seconds at receiver 99 during times when no apnea is indicated, for example, thus indicating receipt of signals not associated with the user's apparatus 15), sound generator 117 is caused to issue an intermittent alarm signal.

As may be appreciated from the foregoing, improved apparatus and methods are provided by this invention for the remote monitoring of selected physiological parameters, the apparatus and methods providing highly reliable transmission of data and ease of operation.

What is claimed is:

1. Used in association with sensing means for sensing a selected physiological parameter of a subject, an apparatus for enabling remote monitoring at a receiving unit of the selected physiological parameter comprising:

processing means for receiving information indicative of the selected physiological parameter from the sensing means and processing said information to provide output indicative of said information;

first transmitter means for receiving said output from said processing means and providing a first radio frequency transmission for receipt by the receiving unit indicative thereof; and second transmitter means operable asynchronously and at a different frequency from said first transmitter means for receiving said output from said processing means and providing a second radio frequency transmission for receipt by the receiving unit indicative thereof.

2. The apparatus of claim 1 wherein said output of said processing means is a data signal including sensed physiological event count data conveying a number of sensed physiological events occurring during a predetermined period, and wherein said first transmitter means provides said first transmission after sensing of each physiological event and wherein said second transmitter means provides said second transmission after each said predetermined period.

3. The apparatus of claim 2 wherein said data signal includes subject status data and signal identification data.

4. The apparatus of claim 3 wherein said selected physiological parameter is respiration, said physiological event is a breath, and said subject status data is one of the occurrence and nonoccurrence of apnea.

5. An apparatus for remote monitoring of respiration of a subject comprising:

a respiration sensor associable with the subject to provide an output indicative of respiration of the subject;

processing means for receiving said output from said sensor and processing said output to provide a first signal indicative of said output, and for selectively providing second and third signals;

first transmitter means for receiving said first and second signals from said processing means and providing a first transmission indicative of said first signal as an output therefrom when enabled by receipt of said second signal;

second transmitter means for receiving said first and third signals from said processing means and providing a second transmission indicative of said first signal as an output therefrom when enabled by receipt of said third signal; and receiver means for receiving said transmissions from said first and second transmitter means and utilizing said transmissions to provide an indication of respiration of the subject.

6. The apparatus of claim 5 wherein said second transmitter means is operated at a different frequency from said first transmitter means.

7. The apparatus of claim 6 wherein said receiver means includes first and second receiving units each for receiving a different one of said first and second transmissions and processing means for processing said received transmissions to provide said indication of respiration of the subject.

8. The apparatus of claim 5 wherein said receiver means includes transmitting means and wherein said indication of respiration of the subject is a third transmission provided from said transmitting means.

9. The apparatus of claim 5 wherein said receiver means includes first and second transmitting means and wherein said indication of respiration of the subject is a third transmission from said first transmitting means indicative of said first signal and a fourth transmission from said second transmitting means indicative of said first signal.

10. The apparatus of claim 9 wherein said output of said respiration sensor is an indication of each breath taken by the subject, wherein said first signal from said processing means is a data signal including sensed breath count data conveying a number of sensed breaths occurring during predetermined periods, wherein said first transmitter means provides said first transmission after sensing of each breath and said first transmitting means of said receiver means provides said third transmission after receipt of said first transmission, and wherein said second transmitter means provides said second transmission after each said predetermined period and said second transmitting means of said receiver means provides said fourth transmission after receipt of said second transmission.

11. The apparatus of claim 5 wherein said first signal from said processing means includes signal identification data, and wherein said receiver means includes validating means for validating said transmissions based on recognition of said signal identification data.

12. An apparatus for remote monitoring of respiration and at least one additional physiological parameter of a subject comprising;

sensing means for sensing respiration and at least one additional physiological parameter of the subject and providing an output indicative thereof;

processing means for receiving said output from said sensing means and providing a signal indicative of said output;

first and second transmitter means providing, asynchronously, first and second transmissions indicative of said signal from said processing means, said first and second transmissions being effective within a first distance;

receiving and retransmitting means for receiving said transmissions from said first and second transmitter means and providing a third transmission indicative of said signal from said processing means, said third transmission being effective within a second distance greater than said first distance; and alerting means for receiving said third transmission and providing an indication to a care giver of subject status.

13. The apparatus of claim 12 wherein said first and second transmissions from said first and second transmitter means are at different frequencies, and wherein said receiving and retransmitting means includes first and second receiving units each configured to receive a different one of said first and second transmissions.

14. The apparatus of claim 12 wherein said receiving and retransmitting means includes first and second transmitters, said first transmitter providing said third transmission and said second transmitter being operable asynchronously and at a different frequency from said first transmitter to provide a fourth transmission indicative of said signal from said processing means, said fourth transmission being received by said alerting means.

15. The apparatus of claim 14 wherein said alerting means includes first and second receivers each configured to receive a different one of said third and fourth transmissions.

16. The apparatus of claim 12 wherein said receiving and retransmitting means includes a processor having memory for processing said transmissions for retransmission and for storage of data indicated therein in memory.

17. The apparatus of claim 12 wherein said alerting means includes visible and audible indicators.

18. The apparatus of claim 12 wherein said signal from said processing means includes breath count data conveying the number of sensed breaths occurring during predetermined periods, and wherein said first transmitter means is enabled by said processing means to provide said first transmission after each sensed breath of the subject, and wherein said second transmitter means is enabled after each said predetermined period by said processing means to provide said second transmission.

19. A method for remote monitoring of a selected physiological parameter of a subject comprising the steps of:

sensing the selected physiological parameter;

processing said sensed physiological parameter to provide a signal indicative of said sensed physiological parameter;

providing a first radio frequency transmission from a first transmission source indicative of said signal at a first frequency;

providing a second radio frequency transmission from a second transmission source indicative of said signal asynchronously and at a different frequency from said first transmission; and receiving said transmissions remotely from the subject at a receiving unit.

20. The method of claim 19 wherein the selected physiological parameter is respiration, wherein said signal is a data signal including sensed breath count data conveying a number of sensed breaths occurring during predetermined periods, wherein said first transmission is provided after each sensed breath, and wherein said second transmission is provided after each said predetermined period.

21. The method of claim 19 further comprising the step of processing said sensed physiological parameter to provide a status signal indicative of subject status with respect to said selected physiological parameter, and wherein said second transmission is also indicative of said status signal.

22. The method of claim 19 further comprising the step of providing an identification signal identifying at least one of validity and source of said transmissions, and wherein said first and second transmissions are also indicative of said identification signal.

23. The method of claim 19 wherein the step of receiving said transmissions includes separately receiving said transmissions, the method further comprising the steps of separately processing said received transmissions and utilizing said processed received transmissions to provide an indication of subject status with respect to the selected physiological parameter.

24. A method for remote monitoring of respiration of a subject comprising the steps of;

sensing each breath, of the subject;

providing a signal indicative of each said sensed breath;

utilizing said signals to provide a count of sensed breaths during selected time periods;

emitting a radio frequency transmission indicative of each said signal;

emitting a radio frequency transmission indicative of said count after each said time period;

receiving said transmissions remotely from the subject; and processing said received transmissions to provide an alert if respiration irregularity is indicated.

25. The method of claim 24 wherein said selected time periods are of a length gauged to identify apnea and wherein said transmission indicative of said count is also indicative of subject status with respect to the occurrence of apnea.

26. The method of claim 24 wherein said transmission indicative of said count is emitted at a frequency different from said transmission indicative of each said signal.

27. The method of claim 26 further comprising the steps of determining if no breaths are sensed during a selected time interval and, if no breaths are sensed during said interval, providing an apnea status indication, and wherein the steps of emitting said transmissions include transmitting said apnea status indication with both of said transmissions.

28. The method of claim 24 wherein the step of receiving said transmissions includes separately receiving said transmissions, and wherein the step of processing said received transmissions includes separately processing said received transmissions.

29. The method of claim 24 further comprising the steps of retransmitting said received transmissions to a more remote receiver.

30. The method of claim 24 including the steps of sensing heart beats of the subject, providing a signal indicative of each said heart beat, and utilizing said signals to provide a count of said heart beats during preselected time periods.

31. The method of claim 30 further comprising the steps of utilizing said count of said heart beats to determine subject status with respect to heart rate, and one of transmitting said status when emitting a transmission indicative of said count of sensed breaths and transmitting said signals indicative of each said heart beat after a said selected time period when no breaths are sensed.

* * * * *